(12) United States Patent
Yoshimura et al.

(10) Patent No.: US 6,458,748 B1
(45) Date of Patent: Oct. 1, 2002

(54) DI- OR TRI-FLUOROMETHANESULFONYL ANILIDE DERIVATIVES, PROCESS FOR THE PREPARATION OF THEM AND HERBICIDES CONTAINING THEM AS THE ACTIVE INGREDIENT

(75) Inventors: Takumi Yoshimura, Shizuoka (JP); Masao Nakatani, Shizuoka (JP); Masatoshi Tamaru, Shizuoka (JP); Takeshi Danjo, Hokkaido (JP); Yukimasa Ono, Shizuoka (JP); Katsutada Yanagisawa, Miyagi (JP)

(73) Assignees: Ihara Chemical Industry Co., Ltd., Tokyo (JP); Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/744,209

(22) PCT Filed: Jul. 28, 1999

(86) PCT No.: PCT/JP99/04043

§ 371 (c)(1),
(2), (4) Date: Jan. 22, 2001

(87) PCT Pub. No.: WO00/06553

PCT Pub. Date: Feb. 10, 2000

(30) Foreign Application Priority Data

Jul. 29, 1998 (JP) .......................................... 10-214635
Aug. 21, 1998 (JP) .......................................... 10-235438

(51) Int. Cl.⁷ ..................... C07D 239/52; A01N 43/54
(52) U.S. Cl. ...................................... 504/243; 544/319
(58) Field of Search .......................... 504/243; 544/319

(56) References Cited

FOREIGN PATENT DOCUMENTS

| EP | 0 363 040 A2 | 4/1990 |
|---|---|---|
| EP | 0 461 079 B1 | 6/1991 |
| JP | 11-60562 A | 3/1999 |
| WO | 93/09099 A2 | 5/1996 |
| WO | 96/41799 A1 | 12/1996 |

*Primary Examiner*—John M. Ford
(74) *Attorney, Agent, or Firm*—Kubovcik & Kubovcik

(57) ABSTRACT

The present invention provides a novel compound which is effective for the removal of a wide variety of weeds including difficult-to-control weeds emerging in paddy field and which is safe to mammals; a process for production thereof; a herbicide containing the compound as an active ingredient; and novel raw material compounds used in said process.

The present invention relates to a di- or trifluoromethanesulfonyl anilide derivative represented by the following general formula:

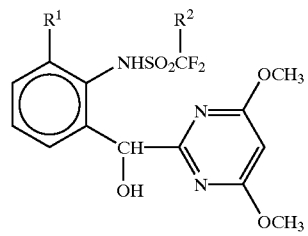

(wherein $R^1$ is a hydrogen atom, an alkyl group or an alkoxyalkyl group; and $R^2$ is a hydrogen atom when $R^1$ is a hydrogen atom or an alkyl group, and is a hydrogen atom or a fluorine atom when $R^1$ is an alkoxyalkyl group), or a salt thereof, both of said derivative and said salt having a herbicidal activity.

9 Claims, No Drawings

US 6,458,748 B1

DI- OR TRI-FLUOROMETHANESULFONYL ANILIDE DERIVATIVES, PROCESS FOR THE PREPARATION OF THEM AND HERBICIDES CONTAINING THEM AS THE ACTIVE INGREDIENT

TECHNICAL FIELD

The present invention relates to a novel di- or trifluoromethanesulfonyl anilide derivative or a salt thereof; a process for production thereof; a herbicide containing said derivative or salt as an active ingredient; and novel raw material compounds used in said process.

BACKGROUND ART

It is known that N-fluoromethanesulfonyl anilide derivatives having a pyrimidinyl-containing group at the 2-position, for example, an N-trifluoromethanesulfonyl anilide derivative of 2-pyrimidinylmethyl-substituted or 2-pyrimidinyloxy or thioxy-substituted aniline has a herbicidal activity (see National Publication of International Patent Application No. 7-501053 and WO 93/09099).

It is also known that an N-trifluoromethanesulfonyl anilide derivative of 2-pyrimidinylhydroxymethyl-substituted aniline has a plant growth-regulating activity (see WO 96/41799).

However, it is not yet known that any of N-di- or trifluoromethanesulfonyl derivatives of aniline having a pyrimidinyl-containing group at the 2-position has a herbicidal activity.

In the cultivation of paddy rice, it has been an important task in recent years to control noxious weeds which emerge in paddy field and which are difficult to control effectively with conventional herbicides, i.e. difficult-to-control weeds. These weeds emerge over a long period of time and, therefore, need to be controlled over a long period of time. Gramineous weeds (other than rice plant) belonging to the same family as rice plant belongs to, for example, *Echinochloa oryzicola* Vasing., etc. emerge over a long period of time as well and grow actively and rapidly; therefore, their control is important as well. No herbicide is developed currently which has a high activity to the above weeds and can control them. Hence, it is desired to develop a chemical agent which has a high herbicidal activity not only to difficult-to-control weeds but also to gramineous weeds, which can control a wide variety of weeds emerging in paddy field, over a long period of time, and which is highly safe to mammals.

Under the above situation, the present invention aims at providing a novel compound which is effective for the removal of a wide variety of weeds including difficult-to-control weeds, emerging in paddy field and which is safe to mammals; a process for production thereof; a herbicide containing the compound as an active ingredient; and novel raw material compounds used in said process.

DISCLOSURE OF THE INVENTION

The present inventors made an intensive study to develop a novel compound having a herbicidal activity. As a result, the present inventors found out that an N-di- or a trifluoromethanesulfonyl derivative of 2-pyrimidinylhydroxymethyl-substituted aniline has a herbicidal activity to a wide variety of weeds at a low dosage, is very effective particularly to gramineous weeds and, moreover, is highly safe to mammals. The present invention has been completed based on the above finding.

The present invention provides a di-, or trifluoromethanesulfonyl anilide derivative represented by the following general formula (I):

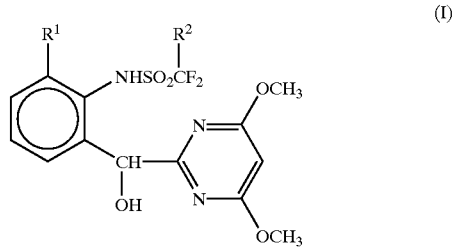

(wherein $R^1$ is a hydrogen atom, an alkyl group or an alkoxyalkyl group; and $R^2$ is a hydrogen atom when $R^1$ is a hydrogen atom or an alkyl group, and is a hydrogen atom or a fluorine atom when $R^1$ is an alkoxyalkyl group), or a salt thereof, both of said derivative and said salt having a herbicidal activity.

Each of the compounds represented by the general formula (I) can be produced, for example, by reacting a 2-substituted aniline derivative (II) with a di- or trifluoromethanesulfonyl halide or trifluoromethanesulfonic-acid anhydride according to the following reaction formula (1):

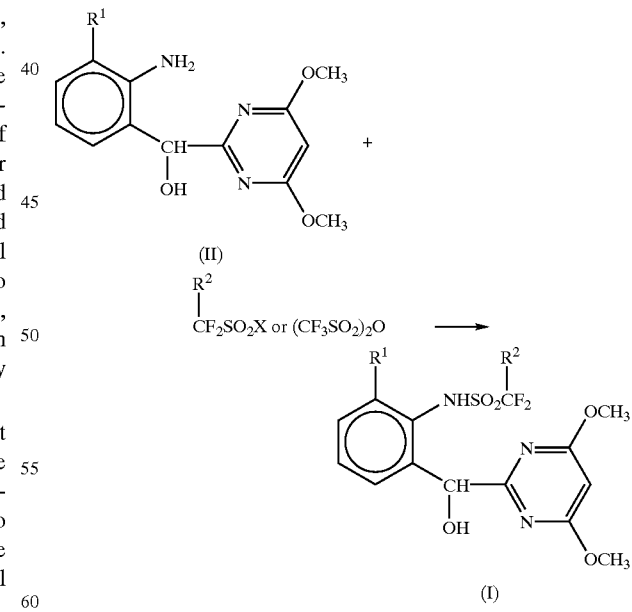

(wherein X is a halogen atom, and $R^1$ and $R^2$ each have the same definition as given above), or by reducing a 2-(4,6-dimethoxypyrimidine-2-ylcarbonyl)-N-di- or trifluoromethanesulfonyl anilide derivative (III) according to the following reaction formula (2):

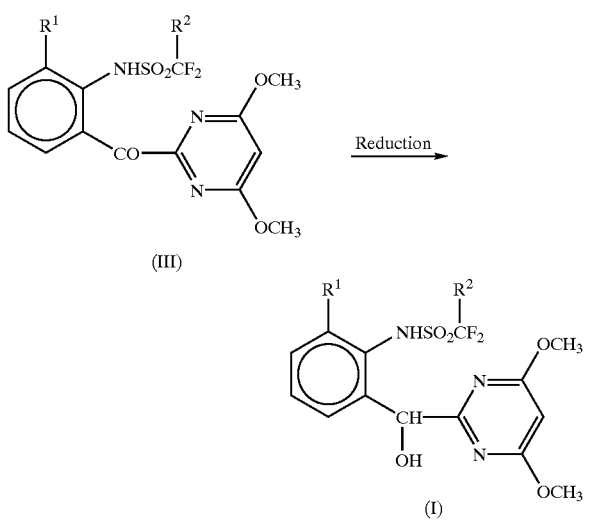

(wherein $R^1$ and $R^2$ each have the same definition as given above).

The compounds represented by the general formula (II) or (III), used in the above production processes are also novel compounds not described in any literature.

In the present compound represented by the general formula (I), $R^1$ is a hydrogen atom, an alkyl group or an alkoxyalkyl group. The alkyl group is preferably a straight chain or branched chain alkyl group having 1 to 5 carbon atoms, such as methyl group, ethyl group, n-propyl group, isopropyl group, n-butyl group, isobutyl group, sec-butyl group, tertbutyl group, n-pentyl group, 1-methylbutyl group, n-hexyl group or the like. The alkoxyalkyl group is preferably a straight chain or branched chain alkoxyalkyl group having 2 to 6 carbon atoms, such as methoxymethyl group, methoxyethyl group, ethoxyethyl group, 3-ethoxypropyl group, 1-methyl-3-methoxybutyl group or the like.

In the present compound represented by the general formula (I), $R^2$ is a hydrogen atom when $R^1$ is a hydrogen atom or an alkyl group, and is a hydrogen atom or a fluorine atom when $R^1$ is an alkoxyalkyl group. When $R^2$ is a hydrogen atom, the present compound represented by the general formula (I) is a difluoromethanesulfonyl anilide derivative; when $R^2$ is a fluorine atom, the present compound represented by the general formula (I) is a trifluoromethanesulfonyl anilide derivative.

The salt of the compound represented by the general formula (I) is a salt between the sulfonylamide group moiety of the compound and a base. As the base, there can be mentioned a sodium salt and a potassium salt.

As the representative examples of the di- or trifluoromethanesulfonyl anilide derivative represented by the general formula (I), there can be mentioned 2-[(4,6-dimethoxypyrimidine-2-yl)hydroxymethyl]-6-methoxymethyl-N-difluoromethanesulfonyl anilide, 2-[(4,6-dimethoxypyrimidine-2-yl)hydroxymethyl]-6-methoxyethyl-N-difluoromethanesulfonyl anilide, 2-[(4,6-dimethoxypyrimidine-2-yl)hydroxymethyl]-6-ethoxymethyl-N-difluoromethanesulfonyl anilide, 2-[(4,6-dimethoxypyrimidine-2-yl)hydroxymethyl]-N-difluoromethanesulfonyl anilide, 2-[(4,6-dimethoxypyrimidine-2-yl)hydroxymethyl]-6-ethyl-N-difluoromethaesulfonyl anilide, 2-[(4,6-dimethoxypyrimidine-2-yl)hydroxymethyl]-6-methoxymethyl-N-trifluoromethanesulfonyl anilide, 2-[(4,6-dimethoxypyrimidine-2-yl)hydroxymethyl]-6-methoxyethyl-N-trifluoromethanesulfonyl anilide, and 2-[(4,6-dimethoxypyrimidine-2-yl)hydroxymethyl]-6-ethoxymethyl-N-trifluoromethanesulfonyl anilide.

The compound represented by the general formula (I) can be produced, for example, by reacting a 2-substituted aniline derivative represented by the general formula (II) with a di- or trifluoromethanesulfonyl halide or trifluoromethanesulfonic acid anhydride according to the above-shown reaction formula (1), or by reducing a 2-(4,6-dimethoxypyrimidine-2-ylcarbonyl)-N-di- or trifluoromethanesulfonyl anilide derivative represented by the general formula (III) according to the above-shown reaction formula (2).

The former process is conducted ordinarily in the presence of a base in an inert solvent such as aliphatic or alicyclic hydrocarbon (e.g. pentane, hexane or cyclohexane), aromatic hydrocarbon (e.g. toluene or xylene), halogenated hydrocarbon (e.g. dichloromethane or chloroform), ether (e.g. diethyl ether, tetrahydrofuran or 1,4-dioxane), ester (e.g. methyl acetate or ethyl acetate), nitrile (e.g. acetonitrile or propionitrile), aprotic polar solvent (e.g. N,N-dimethylformamide, N,N-dimethyl sulfoxide or sulfolane) or mixture thereof.

The base used above is a base conventionally used in a reaction between aniline and acid halide, such as alkali metal hydroxide (e.g. sodium hydroxide or potassium hydroxide), alkaline earth metal hydroxide (e.g. calcium hydroxide) or organic base (e.g. trimethylamine, triethylamine, N,N-dimethylaniline or pyridine).

The reaction temperature is selected in a range of −70 to 250° C., preferably −70 to 40° C. The reaction time differs depending upon the kinds of raw material compounds used, the reaction temperature used, etc. but is about 5 minutes to 7 days.

The latter process is conducted ordinarily in an inert solvent such as alcohol (e.g. methanol or ethanol), ether (e.g. diethyl ether, tetrahydrofuran or 1,4-dioxane), ester (e.g. methyl acetate or ethyl acetate), nitrile (e.g. acetonitrile or propionitrile), aprotic polar solvent (e.g. N,N-dimethylformamide, N,N-dimethyl sulfoxide or sulfolane) or mixture thereof.

The reduction is conducted in the presence of a reducing agent, for example, an alkali metal-hydrogen complex compound (e.g. sodium boron hydride) at a temperature ranging from −70° C. to the boiling point of the solvent used, preferably −20 to 40° C. The reaction time differs depending upon the kinds of the raw material compounds used, the reaction temperature used, etc. but is about 5 minutes to 7 days.

The compounds of the general formula (II) or (III) used as a raw material in the above production processes are as well novel compounds not described in any literature.

These compounds can be easily produced from corresponding 2-(4,6-dimethoxypyrimidine-2-yl)-2-(2-nitrophenyl)acetonitrile (IV) according to the following reaction scheme in accordance with the production process described in, for example, J. Agr. Food. Chem., Vol. 22, No.

6, p. 1111 (1974); J. Chem. Researchers, 1977, p. 186; or Heterocycles, Vol. 38, No. 1, p. 125.

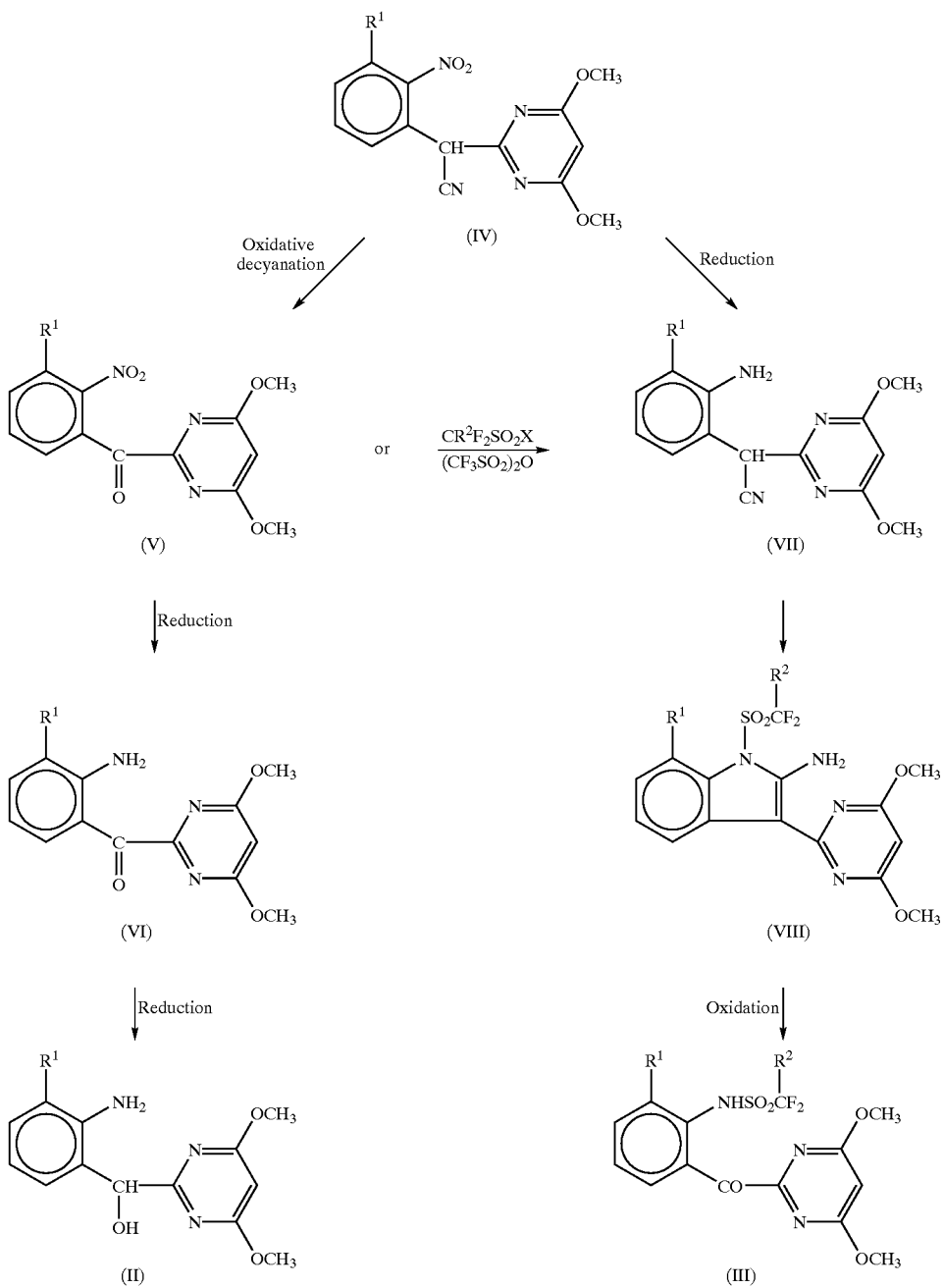

(wherein $R^1$, $R^2$ and X each have the same definition as given above).

The compound of the general formula (II) can be produced, for example, as follows. A 2-nitrophenylacetonitrile derivative is reacted with a 2-halogeno- or alkylsulfonyl-4,6-dimethoxypyrimidine in the presence of a base, or a 2-halogeno-nitrobenzene derivative is reacted with 2-(4,6-dimethoxypyrimidine-2-yl) acetonitrile in the presence of a base, to obtain 2-(4,6-dimethoxypyrimidine-2-yl)-2-(2-nitrophenyl)acetonitrile (IV). The compound (IV) is subjected to oxidative decyanation to obtain a compound of the general formula (V). The nitro group of the compound (V) is reduced to convert it into an amino group to obtain a compound of the general formula (VI). The carbonyl group of the compound (VI) is reduced to a hydroxymethyl group to obtain a compound of the general formula (II).

The oxidative decyanation for converting the compound of the general formula (IV) into the compound of the general formula (V) is conducted by, in a first step, oxidation with an oxidizing agent and, in a second step, treatment with a base.

This reaction is conducted ordinarily in an inert solvent such as aliphatic or alicyclic hydrocarbon (e.g. pentane, hexane or cyclohexane), aromatic hydrocarbon (e.g. toluene or xylene), halogenated hydrocarbon (e.g. dichloromethane or chloroform), ether (e.g. diethyl ether, tetrahydrofuran or 1,4-dioxane), ketone (e.g. acetone or methyl ethyl ketone), ester (e.g. methyl acetate or ethyl acetate), nitrile (e.g. acetonitrile or propionitrile), aprotic polar solvent (e.g. N,N-dimethylformamide, N,N-dimethyl sulfoxide or sulfolane), water, or mixture thereof.

As the oxidizing agent used in the first step, there can be mentioned, for example, organic peracids such as m-chloroperbenzoic acid and the like.

The base used in the second step can freely be selected from the bases conventionally used in the oxidative decyanation of this kind. Such bases include, for example, alkali metal hydroxides such as sodium hydroxide, potassium hydroxide and the like; alkaline earth metal hydroxides such as calcium hydroxide and the like; and organic bases such as trimethylamine, triethylamine, N,N-dimethylaniline, pyridine and the like.

The temperature employed in the above reaction is selected in a range of −70 to 250° C., preferably −20 to 40° C. The reaction time differs depending upon the kinds of the oxidizing agent and base used and the reaction temperature employed, but is ordinarily 5 minutes to 7 days.

The reaction for reducing the nitro group of the compound of the general formula (V) to convert it into an amino group to obtain the aniline derivative of the general formula (VI) can be conducted with a reducing agent in the presence of a catalyst in an inert solvent.

The inert solvent includes, for example, alcohols such as methanol, ethanol and the like; ethers such as diethyl ether, tetrahydrofuran, 1,4-dioxane and the like; esters such as methyl acetate, ethyl acetate and the like; nitrites such as acetonitrile, propionitrile and the like; aprotic polar solvents such as N,N-dimethylformamide, N,N-dimethyl sulfoxide, sulfolane and the like; water; and mixed solvents thereof.

As the reducing agent, there are used, for example, metals such as iron, zinc and tin. As the catalyst, there are used, for example, organic acids such as acetic acid.

The above reaction is conducted at a temperature in a range of ordinarily 20° C. to the boiling point of the solvent used. The reaction time differs depending upon the reducing agent, catalyst and reaction temperature used, but is ordinarily 5 minutes to 7 days.

The reduction for converting the carbonyl group of the compound of the general formula (VI) obtained above, into a hydroxymethyl group can be conducted in the same manner as used in the above-mentioned reduction of the compound of the general formula (III) for production of the present compound (I).

Meanwhile, the compound of the general formula (III) can be produced, for example, by reducing the nitro group of 2-(4,6-dimethoxypyrimidine-2-yl)-2-(2-nitrophenyl) acetonitrile (IV) to convert it into an amino group to obtain a compound of the general formula (VII), then reacting the compound (VII) with di- or trifluoromethanesulfonyl halide or trifluoromethanesulfonic acid anhydride in the presence of a base to produce an indole compound of the general formula (VIII), and subjecting the indole compound (VIII) to oxidation for ring opening.

The reaction for reducing the nitro group of the compound of the general formula (IV) to convert it into an amino group is conducted by hydrogenation in the presence of a catalyst in an inert solvent. The inert solvent can be the same solvent as used in production of the compound of the general formula (V). The catalyst can freely be selected from those conventionally used in catalytic reduction, such as platinum palladium, palladium carbon and the like.

The reaction of the compound of the general formula (VII) with the di- or trifluoromethanesulfonyl halide or trifluoromethanesulfonic acid anhydride can be conducted in the same manner as in the above-mentioned reaction of the compound of the general formula (II) with the di- or trifluoromethanesulfonyl halide or trifluoromethanesulfonic acid anhydride for production of the present compound (I).

The reaction for subjecting the indole derivative of the general formula (VIII) to oxidation for ring opening is conducted by, in first step, treatment of the compound with an oxidizing agent and, in second step, treatment with a base.

This reaction is conducted ordinarily in an inert solvent such as aliphatic or alicyclic hydrocarbon (e.g. pentane, hexane or cyclohexane), aromatic hydrocarbon (e.g. toluene or xylene), halogenated hydrocarbon (e.g. dichloromethane or chloroform), ether (e.g. diethyl ether, tetrahydrofuran or 1,4-dioxane), ketone (e.g. acetone or methyl ethyl ketone), ester (e.g. methyl acetate or ethyl acetate), nitrile (e.g. acetonitrile or propionitrile), aprotic polar solvent (e.g. N,N-dimethylformamide, N,N-dimethyl sulfoxide or sulfolane), water, or mixture thereof.

As the oxidizing agent, there can be mentioned, for example, organic peracids such as m-chloroperbenzoic acid and the like.

As the base, there are used those conventionally used in the reaction of this kind, for example, alkali metal hydroxides such as sodium hydroxide, potassium hydroxide and the like; alkaline earth metal hydroxides such as calcium hydroxide and the like; and organic bases such as trimethylamine, triethylamine, N,N-dimethylaniline, pyridine and the like.

The reaction temperature is selected in a range of −70 to 250° C., preferably −20 to 40° C. The reaction time differs depending upon the base and reaction temperature used, but is ordinarily 5 minutes to 7 days.

The herbicide containing the compound represented by the general formula (I) as an active ingredient can be formulated in various forms conventionally used in general herbicides, such as dust, water dispersible powder, emulsifiable concentrate, fine granules, granules and the like. The compound (I) itself may be used as a herbicide.

The vehicle and additives used in formulation of the above herbicide can freely be selected from those ordinarily used in herbicide formulation, depending upon the application purpose of the herbicide formulated.

As the carrier used in formulation of the above herbicide, there can be mentioned, for example, solid carriers such as talc, bentonite, clay, kaolin, diatomaceous earth, white carbon, vermiculite, calcium carbonate, slake lime, silica sand, ammonium sulfate, urea and the like; and liquid carriers such as isopropyl alcohol, xylene, cyclohexane, methylnaphthalene and the like.

As the surfactant or the dispersant, there can be mentioned, for example, metal alkylbenzenesulfonates, metal dinaphthylmethanedisulfonates, alkyl sulfate salts, alkylarylsulfonic acid salt-formalin condensates, ligninsulfonic acid salts, polyoxyethylene glycol ether, polyoxyethylene alkyl aryl ether and polyoxyethylene sorbitan monoalkylates.

As the auxiliary agent, there can be mentioned, for example, carboxymethyl cellulose, polyethylene glycol and gum arabic.

The herbicide is applied by diluting it in an appropriate concentration and spraying the resulting material, or is applied directly.

The herbicide of the present invention is applied to foliage, soil, water surface, etc.

The amount of the active ingredient in the present herbicide is appropriately determined depending upon the application purpose of the herbicide, but can be selected in a range of 0.01 to 10% by weight, preferably 0.05 to 5% by weight when the herbicide is a dust or granules, and in a range of 1 to 50% by weight, preferably 5 to 30% by weight when the herbicide is an emulsifiable concentrate or a water dispersible powder.

The application amount of the present herbicide differs depending upon the kind of the compound contained in the herbicide, the weed(s) to be removed, the mode of emergence of weed(s), the environmental conditions, the type of the herbicide formulation, etc. However, the amount can be selected in a range of 0.1 g to 5 kg, preferably 1 g to 1 kg per 10 ares in terms of the amount of active ingredient when the herbicide is, for example, a dust or granules and is used directly. When the herbicide is, for example, an emulsifiable concentrate or a water dispersible powder and is used in a liquid form, the amount of active ingredient can be selected in a range of 0.1 to 50,000 ppm, preferably 10 to 10,000 ppm.

The herbicide of the present invention may as necessary be used in combination with an insecticide, a fungicide, other herbicide, a plant growth regulator, a fertilizer, etc.

BEST MODE FOR CARRYING OUT THE INVENTION

Next, the present invention is described in more detail below by way of Examples. However, the present invention is in no way restricted by these Examples.

Reference Example 1

Production of 2-(4,6-dimethoxypyrimidine-2-ylcarbonyl)-N-difluoromethanesulfonyl anilide (1) 50 g (0.31 M) of 2-(2-nitrophenyl)acetonitrile was dissolved in 500 ml of dimethylformamide. Thereto was added 24.7 g (0.62 M) of 60% sodium hydride. The mixture was stirred at room temperature for 2 hours. Then, 68 g (0.31 M) of 4,6-dimethoxy-2-methanesulfonylpyrimidine was added. The mixture was stirred at 80° C. for 1 hour to give rise to a reaction. The reaction mixture was poured into water, followed by neutralization with dilute hydrochloric acid. The mixture was subjected to extraction with ethyl acetate. The extract was washed with water, dried and subjected to vacuum distillation to remove the solvent. The residue was recrystallized from ethanol to obtain 73.3 g (yield: 79%) of 2-(4,6-dimethoxypyrimidine-2-yl)-2-(2-nitrophenyl) acetonitrile as a white powder (melting point: 88 to 89° C.).

Data obtained
$^1$H-NMR 60 MHz CDCl$_3$ TMS 7.5-8.2 (m, 4H), 6.4 (s, 1H), 5.9 (s, 1H), 3.8 (s, 6H)

(2) 3.0 g (10 mM) of the 2-(4,6-dimethoxypyrimidine-2-yl)-2-(2-nitrophenyl)acetonitrile obtained in the above (1) and 0.3 g of 10% palladium carbon were suspended in 100 ml of methanol. While the suspension was stirred at room temperature overnight, hydrogen was added thereto. The solid was removed by filtration. The filtrate was subjected to vacuum distillation to remove methanol. The residue was subjected to silica gel column chromatography (elutant solvent: ethyl acetate/hexane=1/1) for purification to obtain 1.8 g (yield: 67%) of 2-(2-aminophenyl)-2-(4,6-dimethoxypyrimidine-2-yl)acetonitrile as a light yellow candy-like substance.

Data obtained
$^1$H-NMR 60 MHz CDCl$_3$ TMS 6.5-7.6 (m, 4H), 6.9 (s, 1H), 5.3 (s, 1H), 4.6 (br, 2H), 3.9 (s, 6H)

(3) In 100 ml of chloroform were dissolved 4.0 g (14.8 mM) of the 2-(2-aminophenyl)-2-(4,6-dimethoxypyrimidine-2-yl)acetonitrile obtained in the above (2), 2.5 g (31.6 mM) of pyridine and 2.8 g (18.6 mM) of difluoromethanesulfonyl chloride. The solution was stirred at room temperature overnight. The reaction mixture was washed with dilute hydrochloric acid and a saturated aqueous sodium chloride solution, followed by drying over anhydrous magnesium sulfate. The resulting mixture was subjected to vacuum distillation to remove the solvent. The residue was subjected to silica gel column chromatography (elutant solvent: ethyl acetate/hexane=1/3) for separation and purification to obtain 2.0 g (yield: 35%) of 2-amino-1-difluoromethanesulfonyl-3-(4,6-dimethoxypyrimidine-2-yl)indole as a light yellow powder (melting point: 156 to 158° C.).

Data obtained
$^1$H-NMR 300 MHz CDCl$_3$ TMS 8,57 (d, 1H), 7.81 (d, 1H), 7.56 (br, 2H), 7.34 (t, 1H), 7.15 (t, 1H), 6.43 (t, 1H), 5.84 (s, 1H), 4.05 (s, 6H)

(4) In 30 ml of chloroform were dissolved 2.0 g (5.2 mM) of the 2-amino-1-difluoromethanesulfonyl-3-(4,6-dimethoxypyrimidine-2-yl)indole obtained in the above (3) and 2.0 g (5.8 mM) of 50% m-chloroperbenzoic acid. The solution was stirred at room temperature for 12 hours. Then, 15 ml of a 10% aqueous sodium hydroxide solution was added. The mixture was stirred at room temperature for 1 hour. 50 ml of chloroform was added. The organic layer was washed with 5% dilute hydrochloric acid and a saturated aqueous sodium chloride solution, followed by drying. The resulting solution was subjected to vacuum distillation to remove the solvent. The residue was subjected to silica gel column chromatography (elutant solvent: ethyl acetatein-hexane=1/5) for purification to obtain 1.0 g (yield: 52%) of 2-(4,6-dimethoxypyrimidine-2-ylcarbonyl)-N-difluoromethanesulfonyl anilide as a white powder (melting point: 131 to 133° C.).

Data obtained
$^1$H-NMR 300 MHz CDCl$_3$ TMS 11.36 (br, 1H), 7.86 (d, 1H), 7.70 (d, 1H), 7.62 (t, 1H), 7.18 (t, 1H), 6.35 (t, 1H), 6.19 (s, 1H), 3.97 (s, 6H)

Reference Example 2

Production of 2-[(4,6-dimethoxypyrimidine-2-yl) hydroxymethyl]-6-methoxymethylaniline (1) 11.2 g (0.28 M) of 60% sodium hydride was suspended in 100 ml of N,N-dimethylformamide. While the suspension was cooled to 10° C. or lower in an ice water bath and stirred, thereto was dropwise added a solution of 25 g (0.14 M) of 2-(4,6-dimethoxypyrimidine-2-yl)acetonitrile dissolved in 100 ml of N,N-dimethylformamide. After the completion of the dropwise addition, the mixture was stirred at room temperature until there was no evolution of hydrogen. While the mixture was cooled to 10° C. or lower in an ice water bath and stirred, thereto was dropwise added a solution of 28 g (0.14 M) of 2-chloro-6-methoxymethylnitrobenzene dissolved in 100 ml of dimethylformamide. Then, the mixture was stirred at room temperature for 12 hours. The reaction mixture was poured into ice water. The mixture was acidified with 10% hydrochloric acid, followed by extraction with ethyl acetate. The organic layer was washed with a saturated aqueous sodium chloride solution and water, dried and concentrated under reduced pressure. The resulting crystals were washed with a mixed solvent of ethanol and isopropyl ether to obtain 31 g (yield: 64%) of 2-(4,6-dimethoxypyrimidine-2-yl)-2-(3-methoxymethyl-2-nitrophenyl)acetonitrile as a reddish brown powder (melting point: 112 to 113° C).

Data obtained $^1$H-NMR 300 MHz CDCl$_3$ TMS 7.83 (m, 1H), 7.58 (m, 2H), 5.91 (s, 1H), 5.72 (s, 1H), 4.53 (s, 2H), 3.90 (s, 6H), 3.39 (s, 3H)

(2) 11.2 g (0.28 M) of 60% sodium hydride was suspended in 100 ml of N,N-dimethylformamide. While the suspension was cooled to 10° C. or lower in an ice water bath and stirred, there-to was dropwise added a solution of 29 g (0.14 M) of 3-methoxymethyl- 2-nitrophenylacetonitrile dissolved in 100 ml of N,N-dimethylformamide. After the completion of the dropwise addition, the mixture was stirred at room temperature until there was no evolution of hydrogen. While the mixture was cooled to 10° C. or lower in an ice water bath and stirred, thereto was added 30 g (0.14 M) of 4,6-dimethoxy-2-methylsulfonylpyrimidine. The mixture was stirred at room temperature for 12 hours. The reaction mixture was poured into ice water. The mixture was acidified with 10% hydrochloric acid. The resulting crude crystals were collected by filtration, washed with water and a mixed solvent of ethanol and isopropyl ether to obtain 42 g (yield: 87%) of 2-(4,6-dimethoxypyrimidine-2-yl)-2-(3-methoxymethyl-2-nitrophenyl)acetonitrile as a reddish brown powder (melting point: 112 to 113° C.).

Data obtained $^1$H-NMR 300 MHz CDCl$_3$ TMS 7.83 (m, 1H), 7.58 (m, 2H), 5.91 (s, 1H), 5.72 (s, 1H), 4.53 (s, 2H), 3.90 (s, 6H), 3.39 (s, 3H)

(3) In 30 ml of chloroform were dissolved 3.5 g (10 mM) of the 2-(4,6-dimethoxypyrimidine-2-yl)-2-(3-methoxymethyl-2-nitrophenyl)acetonitrile obtained in the above (1) or (2) and 6.0 (17 mM) of 50% m-chloroperbenzoic acid. The solution was stirred at room temperature for 12 hours. Thereto was added 15 ml of a 10% aqueous sodium hydroxide solution, followed by stirring at room temperature for 1 hour. 50 ml of chloroform was added. The organic layer was washed with 5% dilute hydrochloric acid and a saturated aqueous sodium chloride solution, dried, and subjected to vacuum distillation to remove the solvent. The residual crystals were washed with ethanol-diisopropyl ether to obtain 2.8 g (yield: 84%) of (4,6-dimethoxypyrimidine-2-yl)-3-methoxymethyl-2-nitrophenylketone as a white powder (melting point: 111 to 113° C.).

Data obtained $^1$H-NMR 300 MHz CDCl$_3$ TMS 7.90 (d, 1H), 7.72 (t, 1H), 7.61 (d, 1H), 6.13 (s, 1H), 4.78 (s, 2H), 3.90 (s, 6H), 3.47 (s, 3H)

(4) 3.3 g (10 mM) of the (4,6-dimethoxypyrimidine-2-yl)-3-methoxymethyl-2-nitrophenylketone obtained in the above (3), 3 g (54 mM) of an iron powder, 20 ml of water and a mixture of 150 ml of ethyl acetate and 1 ml of acetic acid were subjected to a reaction at 50° C. for 5 hours. The insolubles in the reaction mixture were separated by filtration using a filter aid. The organic layer was washed with a saturated aqueous sodium chloride solution, dried, and subjected to vacuum distillation to remove the solvent. The residual crystals were washed with diisopropyl ether to obtain 2.4 g (yield: 80%) of 2-(4,6-dimethoxypyrimidine-2-ylcarbonyl)-6-methoxymethylaniline as yellow crystals (melting point: 100 to 101° C.).

Data obtained $^1$H-NMR 300 MHz CDCl$_3$ TMS 7.37 (d, 1H), 7.24 (d, 1H), 7.14 (br, 2H), 6.53 (t, 1H), 6.11 (s, 1H), 4.55 (s, 2H), 0.96 (s, 6H), 3.35 (S, 3H)

(5) 3.1 g (10 mM) of the 2-(4,6-dimethoxypyrimidine-2-ylcarbonyl)-6-methoxymethylaniline obtained in the above (4) was dissolved in 50 ml of a 1:1 (by volume ratio) mixed solvent of tetrahydrofuran and water. While the solution was stirred at room temperature, thereto was added 0.6 g (16 mM) of sodium boron hydride. The mixture was stirred at room temperature for 2 hours. 50 ml of ice water was added, followed by extraction with ethyl acetate. The organic layer was washed with a saturated aqueous sodium chloride solution, dried, and subjected to vacuum distillation to remove the solvent. The residual crystals were washed with diisopropyl ether to obtain 2.8 g (yield: 92%) of 2-[(4,6-dimethoxypyrimidine-2-yl)hydroxymethyl]-6-methoxymethylaniline as a white powder (melting point: 40 to 42° C.).

Data obtained $^1$H-NMR 300 MHZ CDCl$_3$ TMS 7.30 (d, 1H), 7.01 (d, 1H), 6.73 (t, 1H), 5.93 (s, 1H), 5.84 (d, 1H), 5.17 (br, 2H), 4.68 (d, 1H), 4.51 (q, 2H), 3.94 (s, 6H), 3.32 (s, 3H)

Reference Example 3

Production of 2-[(4,6-dimethoxypyrimidine-2-yl)hydroxymethyl]-6-ethylaniline (1) The operation of (1) of Reference Example 2 was repeated except that the 2-chloro-6-methoxymethylnitrobenzene used in (1) of Reference Example 2 was replaced by 2-ethyl-6-fluoronitrobenzene, whereby was obtained 2-(4,6-dimethoxypyrimidine-2-yl)-2-(3-ethyl-2-nitrophenyl)acetonitrile as a liver brown powder (melting point: 113 to 114° C.). The yield was 66.6%.

Data obtained $^1$H-NMR 300 MHz CDCl$_3$ TMS 7.73 (d, 1H), 7.50 (t, 1H), 7.36 (d, 1H), 5.92 (s, 1H), 5.52 (s, 1H), 3.91 (s, 6H), 2.56 to 2.76 (m, 2H), 1.26 (t, 3H)

(2) The 2-(4,6-dimethoxypyrimidine-2-yl)-2-(3-ethyl-2-nitrophenyl)acetonitrile obtained in the above (1) was subjected to the same treatment as in (3) of Reference Example 2, whereby was obtained (4,6-dimethoxypyrimidine-2-yl)-3-ethyl-2-nitrophenyl ketone as a white powder (melting point: 116 to 117° C.). The yield was 100%.

Data obtained

1H-NMR 300 MHz CDCl₃ TMS 7.51 to 7.63 (m, 3H), 6.13 (s, 1H), 3.92 (s, 6H), 2.88 (q, 2H), 1.32 (t, 3H)

(3) The (4,6-dimethoxypyrimidine-2-yl)-3-ethyl-2-nitrophenylketone obtained in the above (2) was subjected to the same treatment as in (4) of Reference Example 2, whereby was obtained 2-(4,6-dimethoxypyrimidine-2-ylcarbonyl)-6-ethylaniline as a yellow powder (melting point: 122 to 123° C.). The yield was 64%.

Data obtained

¹H-NMR 300 MHz CDCl₃ TMS 7.25 (d, 2H), 6.67 (br, 2H), 6.56 (t, 1H), 6.11 (s, 1H), 3.95 (s, 6H), 2.56 (q, 2H), 1.30 (t, 3H)

(4) The 2-(4,6-dimethoxypyrimidine-2-ylcarbonyl)-6-ethylaniline obtained in the above (3) was subjected to the same treatment as in (5) of Reference Example 2, whereby was obtained 2-[(4,6-dimethoxypyrimidine-2-yl)hydroxymethyl]-6-ethylaniline as a white powder (melting point: 85 to 86° C.). The yield was 93.7%.

Data obtained

1H-NMR 300 MHz CDCl₃ TMS 7.19 (d, 1H), 7.03 (d, 1H), 6.76 (t, 1H), 5.93 (s, 1H), 5.87 (d, 1H), 4.71 (br, 2H), 4.69 (d, 1H), 3.93 (s, 6H), 2.56 (q, 2H), 1.25 (t, 3H)

EXAMPLE 1

1.0 g (2.7 mM) of the 2-(4,6-dimethoxypyrimidine-2-ylcarbonyl)-N-difluoromethanesulfonyl anilide obtained in Reference Example 1 was dissolved in 50 ml of a 1:1 (by volume ratio) mixed solvent of tetrahydrofuran and water. While the solution was stirred at room temperature; there to was added 0.2 g (5.4 mM) of sodium boron hydride. The mixture was stirred at room temperature for 2 hours. 50 ml of ice water was added, followed by extraction with ethyl acetate. The organic layer was washed with a saturated aqueous sodium chloride solution, dried, and subjected to vacuum distillation to remove the solvent. The residual crystals were washed with diisopropyl ether to obtain 0.8 g (yield: 80%) of 2-[(4,6-dimethoxypyrimidine-2-yl)hydroxymethyl]-N-difluoromethanesulfonyl anilide as a white powder (melting point: 103 to 105° C.).

Data obtained

¹H-NMR 300 MHz CDCl₃ TMS 10.89 (br, 1H), 7.70 (m, 1H), 7.60 (m, 1H), 7.30 (m, 2H), 6.32 (t, 1H), 6.10 (d, 1H), 5.99 (s, 1H), 4.92 (d, 1H), 4.00 (s, 6H)

EXAMPLE 2

In 30 ml of dichloromethane were dissolved 4.0 g (13.1 mM) of the 2-[(4,6-dimethoxypyrimidine-2-yl)hydroxymethyl]-6-methoxymethylaniline obtained in Reference Example 2 and 2.0 g (25.3 mM) of pyridine. While the solution was stirred at −10° C., thereto was dropwise added 3.6 g (23.9 mM) of difluoromethanesulfonyl chloride. The mixture was stirred at room temperature for 7 days. The reaction mixture was poured into ice water, followed by extraction with dichloromethane. The organic layer was washed with 5% dilute hydrochloric acid and a saturated aqueous sodium chloride solution, dried, and subjected to vacuum distillation to remove the solvent. The residue was subjected to silica gel column chromatography (elutant solvent: ethyl acetate/hexane=1/3) for separation and purification to obtain 2.0 g (yield: 36%) of 2-[(4,6-dimethoxypyrimidine-2-yl)hydroxymethyl]-6-methoxymethyl-N-difluoromethanesulfonyl anilide as colorless granular crystals (melting point: 76 to 77° C.).

Data obtained

¹H-NMR 300 MHz CDCl₃ TMS 10.53 (br, 1H), 7.67 (d, 1H), 7.49 (d, 1H), 7.36 (t, 1H), 6.53 (t, 1H), 6.24 (d, 1H), 5.98 (s, 1H), 4.92 (d, 1H), 4.68 (d, 2H), 3.98 (s, 6H), 3.39 (s, 3H)

EXAMPLE 3

In 30 ml of dichloromethane were dissolved 4.0 g (13.8 mM) of the 2-[(4,6-dimethoxypyrimidine-2-yl) hydroxymethyl]-6-ethylaniline obtained in Reference Example 3 and 2.0 g of (25.3 mM) of pyridine. While the solution was stirred at −10° C., thereto was dropwise added 3.6 g (23.9 mM) of difluoromethanesulfonyl chloride. The mixture was stirred at room temperature for 3 days. The reaction mixture was poured into ice water, followed by extraction with dichloromethane. The organic layer was washed with 5% dilute hydrochloric acid and a saturated aqueous sodium chloride solution, dried, and subjected to vacuum distillation to remove the solvent. The residue was subjected to silica gel column chromatography (elutant solvent: ethyl acetate/hexane=1/3) for separation and purification to obtain 2.4 g (yield: 43%) of 2-[(4,6-dimethoxypyrimidine-2-yl)hydroxymethyl]-6-ethyl-N-difluoromethanesulfonyl anilide as a white powder (melting point: 120 to 121° C.).

Data obtained

1H-NMR 300 MHz CDCl₃ TMS 10.34 (br, 1H), 7.56 (q, 1H), 7.27 to 7.32 (m, 2H), 6.40 (t, 1H), 6.27 (d, 1H), 5.97 (s, 1H), 4.93 (d, 1H), 3.98 (s, 6H), 2.95 to 3.07 (m, 1H), 2.76 to 2.89 (m, 1H), 1.23 (q, 3H)

EXAMPLE 4

In 30 ml of dichloromethane were dissolved 4.0 g (13.1 mM) of the 2-[(4, 6-dimethoxypyrimidine-2-yl) hydroxymethyl]-6-methoxymethylaniline obtained in Reference Example 2 and 1.5 g (14.8 mM) of triethylamine. While the solution was stirred at −50° C., thereto was dropwise added 4.0 g (14.2 mM) of trifluoromethanesulfonic acid anhydride. The mixture was stirred at −50 to 0° C. for 3 hours. The reaction mixture was poured into ice water, followed by extraction with dichloromethane. The organic layer was washed with 5% dilute hydrochloric acid and a saturated aqueous sodium chloride solution, dried, and subjected to vacuum distillation to remove the solvent. The residue was subjected to silica gel column chromatography (elutant solvent: ethyl acetate/hexane=1/3) for separation and purification to obtain 3.8 g (yield: 66%) of 2-[(4,6-dimethoxypyrimidine-2-yl)hydroxymethyl]-6-methoxymethyltrifluoromethanesulfonyl anilide as colorless granular crystals (melting point: 91 to 92° C.).

Data obtained

1H-NMR 300 MHz CDCl3 TMS 11.12 (br, 1H), 7.69 (d, 1H), 7.56 (d, 1H), 7.41 (t, 1H), 6.08 (d, 1H), 5.99 (s, 1H), 4.91 (d, 1H), 4.69 (q, 2H), 3.99 (s, 6H), 3.42 (s, 3H)

Test 1

A paddy soil was filled in a plastic pot of 100 cm². Water was taken thereinto and soil puddling was conducted. Seeds of *Echinochloa oryzicola* vasing., *Monochoria vaginalis*

(Burm. f.) Presl var. plantaginea (Roxb.) Solms-Laub., and *Scirpus juncoides* Roxb. subsp. hotarui (Ohwi) *T. Koyama* were sowed at a depth of 0.5 cm. Further, two paddy rice seedlings each of two-leaf stage were transplanted at a depth of 2 cm. Water was filled at a depth of 3 cm. Next day, a water dispersible powder prepared by mixing 10 parts by weight of each of the compounds obtained in Examples 1 to 4, with 0.5 part by weight of a polyoxyethylene octyl phenyl ether, 0.5 part by weight of a sodium salt of a β-naphthalenesulfonic acid-formalin condensate, 20 parts by weight of diatomaceous earth and 69 parts by weight of clay, was diluted with water and dropped onto the water surface so that the amount (g/10 ares) of the active ingredient (each compound) applied became a level shown in Table 1. Development and growth were allowed to take place in a greenhouse. 28 days later, the herbicidal effect of each compound was evaluated according to the following standard. The results are shown in Table 1.

Standard of herbicidal effect (level of suppression of development and growth)

5: Herbicidal effect of 90% or more, injury to paddy rice
4: Herbicidal effect of 70% or more to less than 90%, injury to paddy rice
3: Herbicidal effect of 50% or more to less than 70%, injury to paddy rice
2: Herbicidal effect of 30% or more to less than 50%, injury to paddy rice
1: Herbicidal effect of 10% or more to less than 30%, injury to paddy rice
0: Herbicidal effect of less than 10%, injury to paddy rice For comparison, the same test was conducted using 2-[(4,6-dimethoxypyrimidine-2-yl)hydroxymethyl]-N-trifluoromethanes ulfonyl anilide represented by the following formula (this compound is a compound No. 10-111 in WO 96/41799):

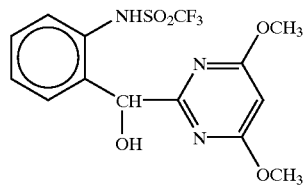

The results are shown in Table 1 as well.

TABLE 1

| Compound | Amount applied (g/10 ares) | Herbicidal effect | | |
|---|---|---|---|---|
| | | Ec | Mo | Sc |
| Example 1 | 25.0 | 5 | 5 | 5 |
| | 6.3 | 4 | 5 | 5 |
| | 1.6 | 3 | 5 | 5 |
| | 0.4 | 1 | 5 | 5 |
| Example 2 | 25.0 | 5 | 5 | 5 |
| | 6.3 | 5 | 5 | 5 |
| | 1.6 | 5 | 5 | 5 |
| | 0.4 | 4 | 5 | 5 |
| Example 3 | 25.0 | 5 | 5 | 5 |
| | 6.3 | 5 | 5 | 5 |
| | 1.6 | 5 | 5 | 5 |
| | 0.4 | 4 | 5 | 5 |

TABLE 1-continued

| Compound | Amount applied (g/10 ares) | Herbicidal effect | | |
|---|---|---|---|---|
| | | Ec | Mo | Sc |
| Example 4 | 25.0 | 5 | 5 | 5 |
| | 6.3 | 5 | 5 | 5 |
| | 1.6 | 5 | 5 | 5 |
| | 0.4 | 2 | 3 | 5 |
| Comparative Compound | 25.0 | 4 | 5 | 5 |
| | 6.3 | 3 | 5 | 5 |
| | 1.6 | 1 | 5 | 5 |
| | 0.4 | 0 | 4 | 5 |

The symbols used in Table 1 refer to the followings.
Ec: *Echinochloa oryzicola* vasing.
Mo: *Monochoria vaginalis* (Burm. f.) *Presl* var. *plantaginea* (Roxb.) Solms-Laub.
Sc: *Scirpus juncoides* Roxb. subsp. hotarui (Ohwi) T. Koyama In the above test, there was substantially no injury to paddy rice.

Test 2

A paddy soil was filled in a plastic pot of 200 cm². Water was taken thereinto and soil puddling was conducted. Seeds of Monochoria vaginalis (Burm. f.) Presl var. plantaginea (Roxb.) Solms-Laub. and *Scirpus juncoides* Roxb. subsp. hotarui (Ohwi) T. Koyama were sowed at a depth of 0.5 cm. Further, a tuber of *Sagittaria pygmaea* Miq. was buried. Water was filled at a depth of 3 cm. Next day, a water dispersible powder containing, as an active ingredient, the compound obtained in Example 1 or the same comparative compound as used in Test 1, which was prepared in the same manner as in Test 1, was diluted with water and dropped onto the water surface so that the amount of the active ingredient (each compound) applied became a level shown in Table 2. For two days starting from the next day, water drainage and feeding each of 2 cm in depth per day were conducted. Then, development and growth were allowed to take place in a greenhouse. On the 28th day from the compound application, the herbicidal effect of each compound was evaluated according to the same standard as used in Test 1. The results are shown in Table 2.

TABLE 2

| Compound | Amount applied (g/10 ares) | Herbicidal effect | | |
|---|---|---|---|---|
| | | Ec | Mo | Sc |
| Example 1 | 5.0 | 5 | 5 | 5 |
| | 2.5 | 5 | 5 | 5 |
| | 1.3 | 4 | 4 | 5 |
| | 0.6 | 2 | 2 | 2 |
| Comparative compound | 5.0 | 5 | 5 | 5 |
| | 2.5 | 3 | 4 | 4 |
| | 1.3 | 1 | 3 | 2 |
| | 0.6 | 0 | 1 | 0 |

The symbols used in Table 2 refer to the followings.
Mo: *Monochoria vaginalis* (Burm. f.) *Presl* var. *plantaginea* (Roxb.) Solms-Laub.
Sc: *Scirpus juncoides* Roxb. subsp. hotarui (Ohwi) T. Koyama
Sa: *Sagittaria pygmaea* Miq.

Test 3

A paddy soil was filled in a plastic pot of 200 cm². Water was taken thereinto and soil puddling was conducted. Seeds of *Echinochloa oryzicola* Vasing. were sowed at a depth of 0.5 cm. Further, two paddy rice seedlings each of two-leaf stage were transplanted at a depth of 2 cm. On the next day (when no germination of *Echinochloa oryzicola* Vasing.

took place) or when the plant reached its three-leaf stage, a water dispersible powder containing, as an active ingredient, each of the compounds obtained in Examples 1 to 3 and the same comparative compound as used in Test 1, which was prepared in the same manner as in Test 1, was diluted with water and dropped onto the water surface so that the amount of the active ingredient (each compound) applied became a level shown in Table 3. Then, development and growth were allowed to take place in a greenhouse. On the 28th day from the compound application, the herbicidal effect of each compound was evaluated according to the same standard as used in Test 1. The results are shown in Table 3.

TABLE 3

| Compound | Amount applied (g/10 ares) | Herbicidal effect (Ec) | |
|---|---|---|---|
| | | Application before germination | Application at 3-leaf stage |
| Example 1 | 5.0 | 5 | 5 |
| | 2.5 | 5 | 4 |
| | 1.3 | 3 | 2 |
| | 0.6 | 2 | 1 |
| | 0.3 | 1 | 0 |
| Example 2 | 5.0 | 5 | 5 |
| | 2.5 | 5 | 5 |
| | 1.3 | 5 | 5 |
| | 0.6 | 5 | 4 |
| | 0.3 | 4 | 3 |
| Example 3 | 5.0 | 5 | 5 |
| | 2.5 | 5 | 5 |
| | 1.3 | 5 | 5 |
| | 0.6 | 5 | 4 |
| | 0.3 | 4 | 2 |
| Comparative Compound | 5.0 | 3 | 1 |
| | 2.5 | 2 | 0 |
| | 1.3 | 1 | 0 |
| | 0.6 | 0 | 0 |
| | 0.3 | 0 | 0 |

The symbol used in Table 3 refers to the following.
Ec: *Echinochloa oryzicola* vasing.

In the above test, there was substantially no injury to paddy rice.

Test 4

A paddy soil was filled in a plastic pot of 200 cm$^2$. Soil puddling was conducted. Seeds of *Echinochloa oryzicola* Vasing. and *Scirpus juncoides* Roxb. subsp. hotarui (Ohwi) T. Koyama were sowed at a depth of 0.5 cm. Tubers of *Sagittaria pygmaea* Miq. and *Cyperus serotinus* Rottb. were buried. Further, two paddy rice seedlings each of two-leaf stage were transplanted at a depth of 2 cm. Water was filled at a depth of 3 cm. Next day, a water dispersible powder containing, as an active ingredient, the compound obtained in Example 4 or the same comparative compound as used in Test 1, which was prepared in the same manner as in Test 1, was diluted with water and dropped onto the water surface so that the amount of the active ingredient (each compound) applied became a level shown in Table 4. Then, development and growth were allowed to take place in a greenhouse. On the 28th day from the compound application, the herbicidal effect and injury to paddy rice, of each compound were evaluated according to the same standard as used in Test 1.

The results are shown in Table 4.

TABLE 4

| Compound | Amount applied (g/10 ares) | Herbicidal effect | | | | Injury to rice |
|---|---|---|---|---|---|---|
| | | Ec | Sc | Sa | Cy | Or |
| Example 4 | 5.0 | 5 | 5 | 5 | 5 | 0 |
| | 2.5 | 5 | 5 | 5 | 5 | 0 |
| | 1.3 | 4 | 5 | 5 | 5 | 0 |
| | 0.6 | 2 | 5 | 4 | 4 | 0 |
| Comparative Compound | 5.0 | 4 | 5 | 5 | 5 | 1 |
| | 2.5 | 2 | 5 | 5 | 5 | 0 |
| | 1.3 | 1 | 5 | 5 | 5 | 0 |
| | 0.6 | 0 | 5 | 5 | 5 | 0 |

The symbols used in Table 4 refer to the followings.
Ec: *Echinochloa oryzicola* Vasing.
Sc: *Scirpus juncoides* Roxb. subsp. hotarui (Ohwi) T. Koyama
Sa: *Saqittaria pygmaea* Mig.
Cy: *cyperus serotinus* Rottb.
Or: *Oryza sativa* L. (paddy rice)

Test 5

A paddy soil was filled in a plastic pot of 200 cm$^2$. Soil puddling was conducted. Seeds of *Echindchloa oryzicola* Vasing. (Ec) were sowed at a depth of 0.5 cm. When Ec reached its one-leaf, two-leaf or three-leaf stage, a water dispersible powder containing, as an active ingredient, the compound obtained in Example 4 or the same comparative compound as used in Test 1, which was prepared in the same manner as in Test 1, was diluted with water and dropped onto the water surface so that the amount of the active ingredient (each compound) applied became a level shown in Table 5. Then, development and growth were allowed to take place in a greenhouse. On the 28th day from the compound application, the herbicidal effect of each compound was evaluated according to the same standard as used in Test 1. The results are shown in Table 5.

TABLE 5

| Compound | Amount applied (g/10 ares) | Herbicidal effect (Ec) Application stage | | |
|---|---|---|---|---|
| | | 1-leaf | 2-leaf | 3-leaf |
| Example 4 | 5.0 | 5 | 5 | 5 |
| | 2.5 | 5 | 5 | 5 |
| | 1.3 | 4 | 3 | 3 |
| Comparative Compound | 5.0 | 3 | 2 | 2 |
| | 2.5 | 1 | 0 | 0 |
| | 1.3 | 0 | 0 | 0 |

As is clear from the above test results, the compound of the present invention shows an excellent herbicidal effect to gramineous weeds, particularly *Echinochloa oryzicola* Vasing. and the like, at a low dosage as compared with known compounds of similar structures.

Test 6 (Teratology Test)

In accordance with the procedure described in "Test guidelines for pesticide (59 Nohsan Notification No. 3850)" issued by the Japan ministry of Agriculture, Forestry and Fisheries, each of the compounds obtained in Examples 1 to 4 and the same comparative compound as used in Test 1 was weighed and suspended in a 0.5% aqueous carboxymethyl cellulose solution; the suspension was orally administered forcibly to 10 SD-strain pregnant rats from the 6th to 15th day of pregnancy. To a control rat group was administered only a 0.5% aqueous carboxymethyl cellulose solution. The amount of each compound to be administered was determined by a preliminary test. That is, each compound was administered to three SD-strain nonpregnant rats for 10 consecutive days and the maximum tolerated dose was estimated; this dose was taken as the amount of each compound to be administered. On the 20th day of pregnancy, each tested rat underwent Caesarian operation and there were conducted fetal examination (number of alive fetuses, number of embryonic resorption, number of dead fetuses, sex ratio, weight of fetus and external abnormalities of fetus). Further, the fetuses were fixed in 70% ethanol, their soft tissues were macerated in potassium hydroxide, their skeletons were dyed with Alizarin Red S, and obserbation of skeleton was conducted. The results are shown in Table 6. In these tests, a case of no abnormality was reported as "pass" and a case of any abnormality was reported as "fail".

TABLE 6

| Compound | Amount applied (mg/kg/day) | Number of tested rats | Test results |
| --- | --- | --- | --- |
| Example 1 | 450 | 10 | Pass |
| Example 2 | 550 | 10 | Pass |
| Example 3 | 1000 | 10 | Pass |
| Example 4 | 400 | 10 | Pass |
| Comparative compound | 90 | 10 | Fail |
| Control | 0 | 10 | Pass |

Thus, when each of the compounds obtained in Examples 1 to 4 was administered orally to SD-strain pregnant rats consecutively from the 6th to the 15th day of pregnancy, decrease in fetus weight was seen in the rat group to which the comparative compound was administered, in the fetal examination. In the gross examination of fetus, external malformation, i.e. the ectrodactyly and brachydactyly of front leg were seen in the rat group to which the comparative compound was administered; these phenomena were not seen with any of the compounds obtained in Examples 1 to 4.

Formulation Example 1

10 parts by weight of the compound obtained in Example 1 was mixed with 0.5 part by weight of a polyoxyethylene octyl phenyl ether, 0.5 part by weight of a sodium salt of naphthalenesulfonic acid-formalin condensate, 20 parts by weight of diatomaceous earth and 69 parts by weight of clay. The mixture was powderized to prepare a water dispersible powder.

Formulation Example 2

10 parts by weight of the compound obtained in Example 2 was mixed with 0.5 part by weight of a polyoxyethylene octyl phenyl ether, 0.5 part by weight of a sodium salt of β-naphthalenesulfonic acid-formalin condensate, 20 parts by weight of diatomaceous earth, 5 parts by weight of white carbon and 64 parts by weight of calcium carbonate. The mixture was powderized to prepare a water dispersible powder.

Formulation Example 3

10 parts by weight of the compound obtained in Example 3 was mixed with 0.5 part by, weight of a polyoxyethylene octyl phenyl ether, 0.5 part by weight of a sodium salt of β-naphthalenesulfonic acid-formalin condensate, 20 parts by weight of diatomaceous earth, 5 parts by weight of white carbon and 64 parts by weight of clay. The mixture was powderized to prepare a water dispersible powder.

Formulation Example 4

30 parts by weight of the compound obtained in Example 1 was mixed with 60 parts by weight of a 1:1 (by volume ratio) mixture of xylene and isophorone and 10 parts by weight of a 1:1:1 (by volume ratio) mixture of a polyoxyethylene sorbitan alkylate, a polyoxyethylene alkyl aryl polymer and an alkyl aryl sulfonate, to prepare a emulsifiable concentrate.

Formulation Example 5

10 parts by weight of water was added to 10 parts by weight of the compound obtained in Example 3, 80 parts by weight of a 1:3 (by weight ratio) mixed filler of talc and bentonite, 5 parts by weight of white carbon and 5 parts by weight of a 1:1:1 (by volume ratio) mixture of a polyoxyethylenesorbitan alkylate, a polyoxyethylene alkyl aryl polymer and an alkyl aryl sulfonate. The mixture was well kneaded to make a paste. The paste was extrudated through the 0.7-mm openings of a sieve and dried. The dried material was cut into lengths of 0.5 to 1 mm to prepare granules.

Formulation Example 6

10 parts by weight of the compound obtained in Example 4 was mixed with 0.5 part by weight of a polyoxyethylene octyl phenyl ether, 0.5 part by weight of a sodium salt of β-naphthalenesulfonic acid-formalin condensate, 20 parts by weight of diatomaceous earth and 69 parts by weight of clay. The mixture was powderized to prepare a water dispersible powder.

Formulation Example 7

10 parts by weight of the compound obtained in Example 4 was mixed with 0.5 part by weight of a polyoxyethylene octyl phenyl ether, 0.5 part by weight of a sodium salt of β-naphthalenesulfonic acid-formalin condensate, 20 parts by weight of diatomaceous earth, 5 parts by weight of white carbon and 64 parts by weight of clay. The mixture was powderized to prepare a water dispersible powder.

Formulation Example 8

10 parts by weight of the compound obtained in Example 4 was mixed with 0.5 part by weight of a polyoxyethylene octyl phenyl ether, 0.5 part by weight of a sodium salt of β-naphthalenesulfonic acid-formalin condensate, 20 parts by weight of diatomaceous earth, 5 parts by weight of white carbon and 64 parts by weight of calcium carbonate. The mixture was powderized to prepare a water dispersible powder.

Formulation Example 9

30 parts by weight of the compound obtained in Example 4 was mixed with 60 parts by weight of a 1:1 (by volume ratio) mixture of xylene and isophorone and 10 parts by weight of a 1:1:1 (by volume ratio) mixture of a polyoxyethylene sorbitan alkylate, a polyoxyethylene alkyl aryl polymer and an alkyl aryl sulfonate, to prepare a emulsifiable concentrate.

Formulation Example 10

10 parts by weight of water was added to 10 parts by weight of the compound obtained in Example 4, 80 parts by weight of a 1:3 (by weight ratio) mixed filler of talc and bentonite, 5 parts by weight of white carbon and 5 parts by weight of a 1:1:1 (by volume ratio) mixture of a polyoxyethylene sorbitan alkylate, a polyoxyethylene alkyl aryl polymer and an alkyl aryl sulfonate. The mixture was well kneaded to make a paste. The paste was extruded through the 0.7-mm openings of a sieve and dried. The dried material was cut into lengths of 0.5 to 1 mm to prepare granules.

Industrial Applicability

The present compound has a herbicidal activity at a low dosage to a variety of weeds over various seasons, has a high controlling effect particularly to gramineous weeds, is very safe to mammals (for example, causes no malformation); and is a novel substance useful as a herbicide or as a raw material for production thereof.

What is claimed is:

1. A di- or tri-fluoromethanesulfonyl anilide derivative represented by the following formula:

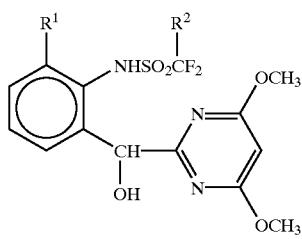

(wherein $R^1$ is a hydrogen atom, an alkyl group or an alkoxyalkyl group; and $R^2$ is a hydrogen atom when $R^1$ is a hydrogen atom or an alkyl group, and is a hydrogen atom or a fluorine atom when $R^1$ is alkoxyalkyl group), or a salt thereof.

2. A di- or trifluoromethanesulfonyl anilide derivative or a salt thereof according to claim 1, wherein $R^1$ is a hydrogen atom.

3. A di- or trifluoromethanesulfonyl anilide derivative or a salt thereof according to claim 1, wherein $R^1$ is an alkyl group.

4. A di- or trifluoromethanesulfonyl anilide derivative or a salt thereof according to claim 3, wherein the alkyl group is an ethyl group.

5. A di- or trifluoromethanesulfonyl anilide derivative or a salt thereof according to claim 1, wherein $R^1$ is an alkoxyalkyl group.

6. A di- or trifluoromethanesulfonyl anilide derivative or a salt thereof according to claim 5, wherein the alkoxyalkyl group is a methoxymehtyl group.

7. A herbicide composition comprising, as an active ingredient, a di- or trifluoromethanesulfonyl anilide derivative represented by the following formula:

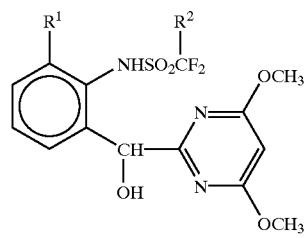

(wherein $R^1$ is a hydrogen atom, an alkyl group or an alkoxyalkyl group; and $R^2$ is a hydrogen atom when $R^1$ is a hydrogen atom or an alkyl group, and is a hydrogen atom or a fluorine atom when $R^1$ is an alkoxyalkyl group), or a salt thereof, and an inert carrier.

8. A 2-substituted aniline derivative represented by the following formula:

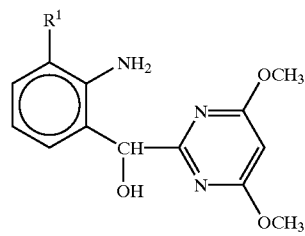

(wherein $R^1$ is a hydrogen atom, and alkyl group or an alkoxyalkyl group).

9. A di- or tri-fluoromethanesulfonyl anilide derivative represented by the following formula:

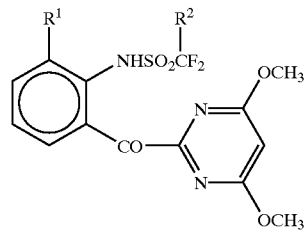

(wherein $R^1$ is a hydrogen atom, an alkyl group or an alkoxyalkyl group; and $R^2$ is a hydrogen atom when $R^1$ is a hydrogen atom or an alkyl group, and is a hydrogen atom or a fluorine atom when $R^1$ is an alkoxyalkyl group).

* * * * *